United States Patent [19]
Christensen

[11] Patent Number: 4,808,921
[45] Date of Patent: Feb. 28, 1989

[54] PARAMAGNETIC GAS ANALYZER USING DC AND AC MAGNETIC FIELDS

[75] Inventor: Jorgen Christensen, Birkerød, Denmark

[73] Assignee: Aktieselskabet Bruel & Kjar, Naerum, Denmark

[21] Appl. No.: 52,613

[22] Filed: May 20, 1987

[30] Foreign Application Priority Data

May 27, 1986 [DK] Denmark ............................ 2476/86

[51] Int. Cl.⁴ ...................... G01N 27/74; G01R 33/12
[52] U.S. Cl. .................................. 324/204; 73/27 A; 128/203.14
[58] Field of Search .................... 324/204, 228; 73/23, 73/27 A, 27 R; 310/111; 335/230; 128/203.14, 203.17, 203.25, 203.26, 203.12

[56] References Cited

U.S. PATENT DOCUMENTS

| | | |
|---|---|---|
| 3,191,425 | 6/1965 | Waters . |
| 3,240,051 | 3/1966 | Lenfant . |
| 3,287,959 | 11/1966 | Karl-Friedrich Luft . |
| 3,302,448 | 2/1967 | Mocker . |
| 3,584,499 | 6/1971 | Hummel . |
| 3,866,461 | 2/1975 | Machytka . |
| 3,879,658 | 4/1975 | Hummel ............................. 324/201 |
| 3,881,152 | 4/1975 | Tasaki ................................. 324/204 |
| 4,173,975 | 11/1979 | DeLong et al. ................ 324/204 X |
| 4,403,186 | 9/1983 | Kotani et al. . |
| 4,563,894 | 1/1986 | Karrer ........................... 73/27 A X |
| 4,633,705 | 1/1987 | Merilainen et al. . |
| 4,683,426 | 7/1987 | Hummel ............................. 324/204 |

FOREIGN PATENT DOCUMENTS

| | | |
|---|---|---|
| 859387 | 12/1952 | Fed. Rep. of Germany . |
| 1124735 | 3/1962 | Fed. Rep. of Germany . |
| 1951532 | 7/1973 | Fed. Rep. of Germany . |
| 2058633 | 12/1977 | Fed. Rep. of Germany . |

OTHER PUBLICATIONS

"Delta Trac Metabolic Monitor", Dater Instrumentarium Corp. June 1987, Catalog Brochure.

Primary Examiner—Reinhard J. Eisenzopf
Assistant Examiner—Warren S. Edmonds
Attorney, Agent, or Firm—Scully, Scott, Murphy and Presser

[57] ABSTRACT

Paramagnetic gas analyzer comprising an electromagnet with an almost closed ferromagnetic circuit and a gap, including a measuring chamber with inlet and outlet lines for the gas to be analyzed as well as a gas of known magnetic susceptibility where devices are provided which measure the differential gas pressures in the respective lines by supplying an AC current to the electromagnetic. According to the present invention it is shown, how the power consumption can be considerably reduced. This object is achieved by superimposing a DC magnetic field generated by means of a permanent magnet onto the AC magnetic field. The amplitude of the measuring result depends on the product of the AC field and the DC field. If the DC field is strong enough, the AC field and thus the supplied power can be reduced accordingly. The latter also facilitates the filtering off of predetermined, undesirable signals.

4 Claims, 3 Drawing Sheets

PARAMAGNETIC GAS ANALYZER USING DC AND AC MAGNETIC FIELDS

FIELD OF THE INVENTION

This invention relates to an apparatus determining the concentration of a paramagnetic gas by measuring its pressure when subjected to an AC magnetic field, said apparatus comprising an electromagnet with an almost closed ferromagnetic circuit and a gap, including a measuring chamber with inlet and outlet lines for the gas to be analyzed as well as a gas of known magnetic susceptibility where devices are provided which measure the differential gas pressures in the respective lines by supplying an AC current to the electromagnet.

BACKGROUND ART

Known apparatuses of this kind require a strong AC magnetic field in order to achieve an acceptable measuring signal. The magnetic field is generated either by means of an electromagnet, mechanically by means of a reluctance modulator (U.S. Pat. No. 3,240,051) or by means of a rotating magnetic system. A mechanic system can only operate at comparatively low frequencies, e.g. 10 Hz, and is thus sensitive to noise and vibrations. Higher frequencies can be achieved with an electromagnet, e.g. 100–200 Hz, which, however, requires a comparatively high electric power input.

SUMMARY OF THE INVENTION

According to the present invention it is shown, how the power consumption can be considerably reduced. This object is achieved by superimposing a DC magnetic field generated by means of a permanent, magnet onto the AC magnetic field.

The amplitude of the measuring result depends on the product of the AC field and the DC field. If the DC field is strong enough, the AC field and thus the supplied power can be reduced accordingly. The latter also facilitates the filtering off of predetermined undesirable signals.

If it is desired to employ a ferromagnetic circuit, including a ferrite, the magnetic DC circuit can be a local circuit. Thus a saturation of the ferrite core is avoided. The local magnetic circuit can e.g. be generated by means of two annular permanent magnets surrounding the measuring chamber and being separated by a disc of soft iron.

BRIEF DESCRIPTION OF DRAWINGS

The invention will be described below with reference to the accompanying drawings, in which.

DESCRIPTION OF PREFERRED EMBODIMENTS

Figure 1:
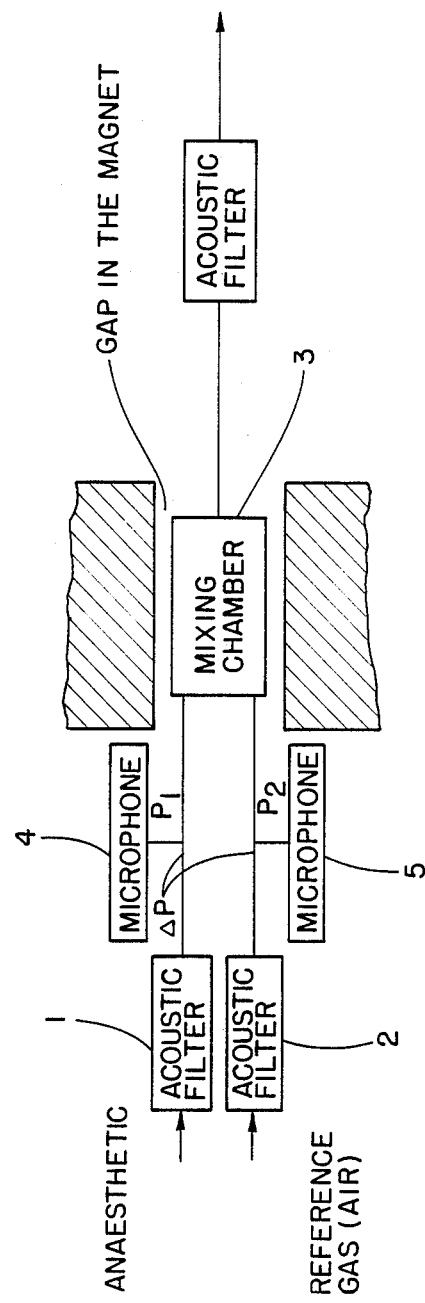
FIG. 1 shows an apparatus for measuring the magnetic susceptibility of a gas.

According to the present invention an apparatus is provided for monitoring the composition of anesthetics inhaled and exhaled by a patient under anesthesia. The gases desired to be measured are $O_2$, $N_2O$, $CO_2$ and anesthetics, such as halothane, enflurane or isoflurane. All gases with the exception of oxygen can be measured photoacousticly. The oxygen content can, however, be monitored by an apparatus using the special paramagnetic characteristics of oxygen. The magnetic susceptibility of oxygen is comparatively large, i.e. 200 times larger than e.g. the susceptibility of $N_2O$. Thus, a measuring of the susceptibility of anesthetics indicates almost exclusively the oxygen concentration. The principle of the measurement is shown in FIG. 1. The anesthetic and a reference gas are separately delivered through the acoustic filters 1 and 2 into the mixing chamber 3. The chamber is situated in a magnetic field. In case of a paramagnetic gas the pressure in the magnetic field is higher than outside the field. The pressure difference is $$P = \rho \chi \frac{B^2}{2\mu_O}$$

with $\rho$ being the specific density of oxygen and
$\chi$ being its specific magnetic susceptibility.

With an AC magnetic field in the measuring chamber an acoustic differential signal is generated between two microphones 4 and 5, respectively connected to the line feeding the anesthetic and the one feeding the reference gas. The differential signal is $$\Delta p_{RMS} = \Delta \rho \cdot \chi \frac{B^2_{RMS}}{2\mu_O}$$

where $\Delta \rho$ is the difference between the oxygen concentration of the anesthetic and the reference gas.

In order to achieve an acceptable measuring signal a strong magnetic field, however, is required. With a B-field of 0.35 T, for example, a measuring signal of 50 dB is obtained at a oxygen concentration of 21%. The AC field is generated by means of an electromagnet. Such an electromagnet generates measuring frequencies of up to 100–200 Hz. The necessary electric power is, however, high and the apparatus thus comparatively large.

The power consumption can, however, be considerably reduced by superimposing a DC field generated by a permanent magnet onto the AC field.

Figure 2:
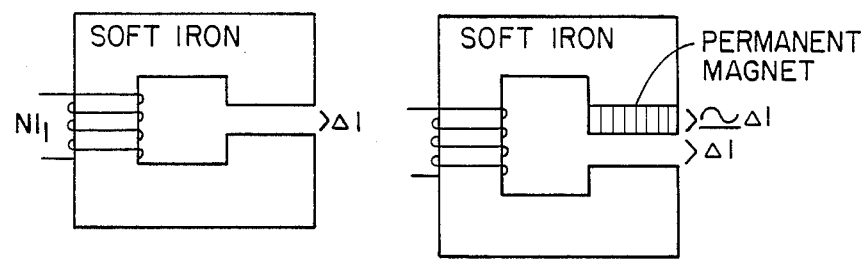
FIG. 2 illustrates how a DC magnetic field generated by a permanent magnet is superimposed onto an AC magnetic field.

FIG. 2 shows an electromagnet with and without a permanent magnet. Without the permanent magnet a signal is generated at the frequency $2\omega$, which is proportional to $B_1^2/2$, where $B_1$ is the amplitude of the AC magnetic field in the gap.

A magnetic circuit with a permanent magnet generates a signal proportional to $2B_0 b_0$, where $b_0$ is the amplitude of the AC magnetic field in the gap and $B_0$ is the DC magnetic field.

If $B^2_1/2 = 2B_0 b_0$ the measuring signal is the same in both cases, which means that the supplied energy can be reduced by the factor $B_0/b_0$. A desired signal of 50 db with an oxygen concentration of 21% requires that $B_1 = 0.35$ T. In a system using a permanent magnet, the same signal can, for example, be obtained with $B_0 = 0.6$ T and $b_0 = 0.05$ T. The supplied electric energy can thus be reduced by the factor $$B_0/b_0 = 0.6/0.05 = 12.$$

The DC field is, however, not to be so strong as to saturate the soft iron. Furthermore, using normal soft iron, the maximal frequency is limited.

If a higher frequency is desired a ferrite core has to be employed. This material possesses, however, a small saturation induction. In order to avoid saturation of the ferrit a local DC circuit is employed. Thus DC current does not flow through the ferrite.

Figure 3:
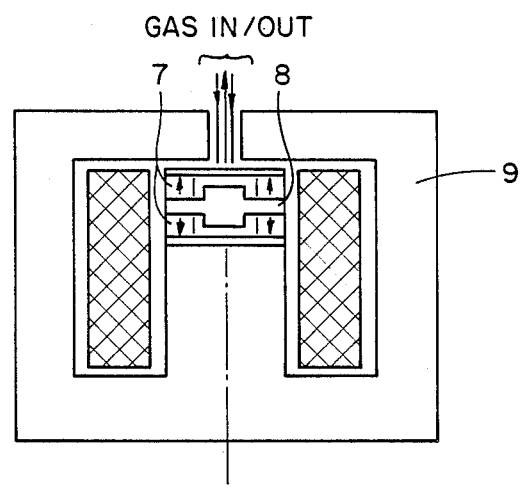
FIG. 3 illustrates how a local DC magnetic field is superimposed onto an AC magnetic field.

FIG. 3 shows a magnetic system with such a local magnetic circuit. The local magnetic circuit is generated by means of two annular permanent magnets 7, surrounding the measuring chamber and being separated by a soft iron disc 8. The outer ferrite 9 effectively screens off the stray field from the gap. Since the ferrite 9 only carries an AC field, the remaining AC field is pure AC. The stray field influences the microphones 4 and 5 via their nickel membrane, which causes the generation of a false signal at a frequency of $2\omega$, i.e. twice the measuring frequency.

Furthermore, the magnetic powers in a magnetic system generate vibrations which, via microphones, cause another false signal at the frequency $2\omega$. Neither does this signal influence the measuring signal at $\omega$.

Figure 4:
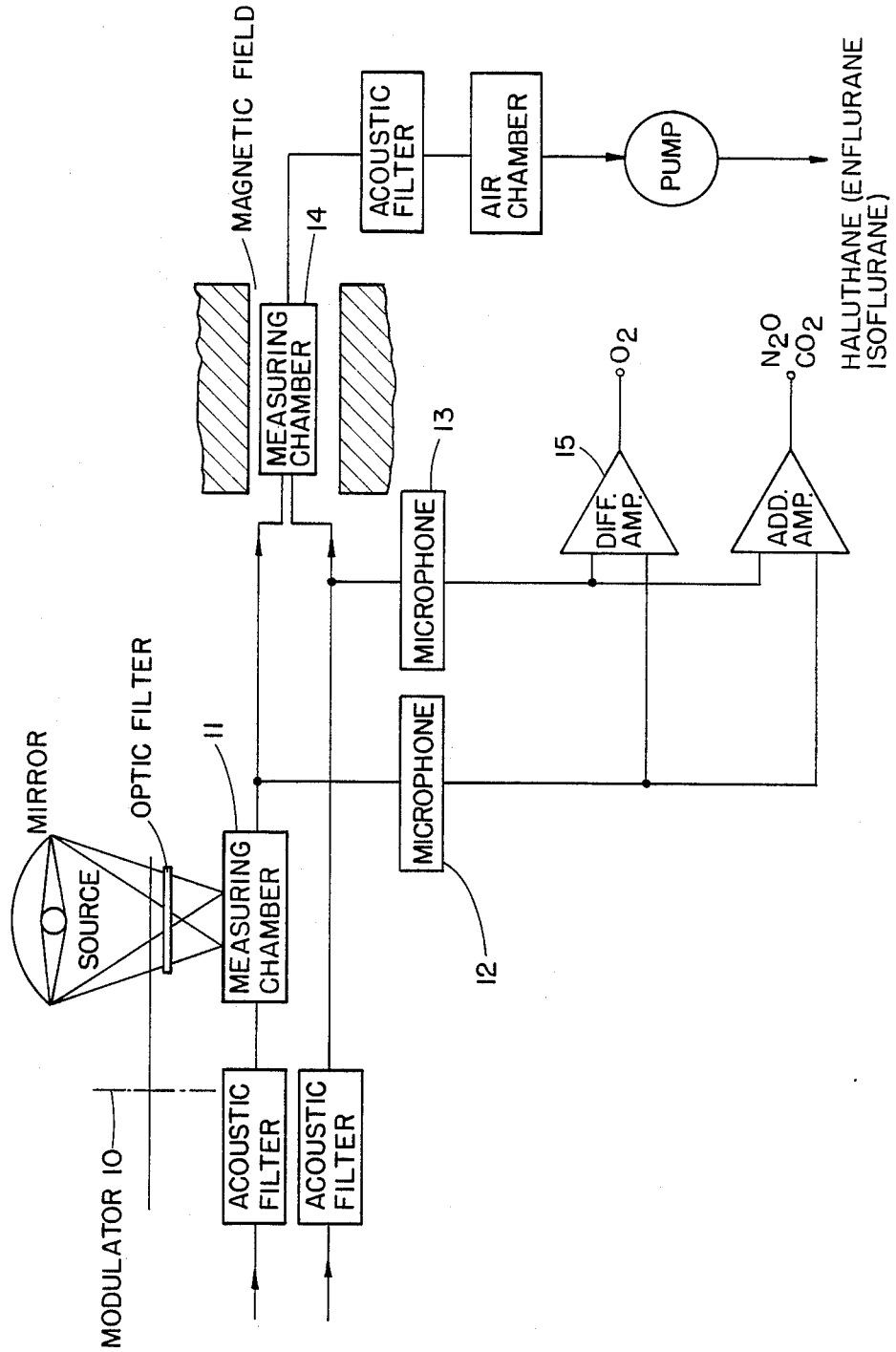
FIG. 4 shows a paramagnetic measuring device combined with a photoacoustic measuring device.

FIG. 4 illustrates a combined photoelectric and paramagnetic measuring apparatus including a measuring chamber and a light source. Between the measuring chamber and the light source there is a modulator 10 and a filter. The modulator 10 is a rotating disc with holes. The modulator causes a pulsating light beam to be sent to the measuring chamber 11. As a result of the absorption in the measuring chamber 11 and the resulting heating of the enclosed gases an acoustic signal is generated in the measuring chamber 11. This signal is measured by means of the microphone 12 communicating with the measuring chamber 11. The gases from the measuring chamber 11 together with a reference gas are fed into another measuring chamber 14 in the gap of a magnet. The pressure in each of the lines is measured by means of the microphones 12 and 13. The electric signals from the microphones 12 and 13 are fed into a differential amplifier 15, indicating the oxygen concentration. An special advantage of this measuring arrangement is the use of the same microphones 12 and 13 for both measuring methods. The photoelectric measuring method is especially suitable for measuring the contents of $N_2O$, $CO_2$ and anesthetics, whereas the paramagnetic measuring method is suitable for measuring oxygen content.

I claim:

1. Apparatus determining the concentration of a paramagnetic gas by measuring its pressure when subjected to an AC magnetic field, said apparatus comprising an AC electromagnet with an almost closed ferromagnetic circuit, a permanent magnet and a gap, a chamber positioned within said gap inlet and outlet lines for the gas to be analyzed as well as a gas of known magnetic susceptibility and means for measuring differential gas pressures in the respective lines created when the gas to be analyzed and the gas of known magnetic susceptibility are subjected to a combined AC and DC magnetic field generated by the electromagnet having an AC current winding and the permanent magnet wherein the DC magnetic field is superimposed onto the AC magnetic field by the permanent magnet.

2. Apparatus as in claim 1 wherein the magnetic DC field is generated by means of two annular permanent magnets surrounding the measuring chamber and being separated by a disc of soft iron.

3. Apparatus determining the concentration of a paramagnetic gas by measuring its pressure when subjected to an AC magnetic field, said apparatus comprising an AC electromagnet with an almost closed ferromagnetic circuit, a local circuit and a gap, a chamber positioned within said gap with inlet and outlet lines for the gas to be analyzed as well as a gas of known magnetic susceptibility and means for measuring differential gas pressures in the respective lines created when the gas to be analyzed and the gas of known magnetic susceptibility are subjected to a combined AC and DC magnetic field generated by the electromagnet having an AC current winding and a DC current applied to the local circuit wherein the DC magnetic field is superimposed onto the AC magnetic field by the local circuit.

4. Apparatus according to any of claims 1-3 used in connection with a photo acoustic gas analyzer.

* * * * *